United States Patent [19]
Mochizuki et al.

[11] Patent Number: 5,514,686
[45] Date of Patent: May 7, 1996

[54] USE OF MACROLIDE COMPOUNDS FOR EYE DISEASES

[75] Inventors: Manabu Mochizuki, Fukuoka; Yoichi Iwaki, Kurume, both of Japan

[73] Assignee: Fujisawa Pharmaceutical Co., Ltd., Osaka, Japan

[21] Appl. No.: 133,194

[22] PCT Filed: Apr. 24, 1992

[86] PCT No.: PCT/JP92/00545

§ 371 Date: Apr. 1, 1994

§ 102(e) Date: Apr. 1, 1994

[87] PCT Pub. No.: WO92/19278

PCT Pub. Date: Nov. 12, 1992

[30] Foreign Application Priority Data

Apr. 26, 1991 [GB] United Kingdom ............... 9109060
Oct. 11, 1991 [GB] United Kingdom ............... 9121661

[51] Int. Cl.$^6$ .................... A61K 31/395; C07D 498/16
[52] U.S. Cl. ............................. 514/297; 540/456
[58] Field of Search ........................... 514/291

[56] References Cited

U.S. PATENT DOCUMENTS

| | | | |
|---|---|---|---|
| 4,956,352 | 9/1990 | Okuhara et al. | 514/291 |
| 5,011,844 | 4/1991 | Fehr | 514/291 |
| 5,212,155 | 5/1993 | Calne | 514/291 |
| 5,308,847 | 5/1994 | Calne | 514/291 |
| 5,387,589 | 2/1995 | Kulkarni | 514/291 |

FOREIGN PATENT DOCUMENTS

| | | | |
|---|---|---|---|
| 0184162 | 6/1986 | European Pat. Off. | 514/291 |
| 0356399 | 2/1990 | European Pat. Off. | |
| 0402931 | 12/1990 | European Pat. Off. | 514/291 |
| 0406791A2 | 1/1991 | European Pat. Off. | |
| 8133194 | 6/1992 | United Kingdom | 514/291 |
| WO89/05304 | 6/1984 | WIPO | 514/291 |
| WO88/00193 | 12/1988 | WIPO | 514/291 |
| WO90/09790 | 9/1990 | WIPO | |
| WO90/09760 | 9/1990 | WIPO | 514/450 |
| WO90/14826 | 12/1990 | WIPO | |

OTHER PUBLICATIONS

Kobayasshi et al. "Transplantation Proceedings" vol. XXI, No. 1, (1989) pp. 3156–3158.
Transplantation Proceedings, vol. 21, No. 1, Feb. 1989, C. Kobayashi, et al., "Supression of Corneal Graft Rejection in Rabbits By a New Immunosuppressive Agent, FK–506", pp. 3156–3158.
The Journal of Immunology, vol. 146, No. 7, Apr. 1, 1991, pp. 2374–2381, Amato de Paulis, et al., "FK–506, A Potent Novel Inhibitor of the Release of Proinflammatory Mediators from Human FceRI[+] Cells[1]".
The Journal of Allergy and Clinical Immunology, vol. 87, No. 1, Part 2, Jan. 1991, p. 207.

*Primary Examiner*—Robert T. Bond
*Attorney, Agent, or Firm*—Oblon, Spivak, McClelland, Maier & Neustadt

[57] ABSTRACT

Macrolide compounds such as the FR-900506 and its related compounds are provided for the prevention or treatment of eye diseases, particularly, allergic conjunctivitis. Composition containing such compounds is also disclosed.

4 Claims, No Drawings

USE OF MACROLIDE COMPOUNDS FOR EYE DISEASES

DESCRIPTION

NEW USE

This invention relates to a new use of macrolide compounds for eye diseases. More specifically, this invention relates to a new use of macrolide compounds for eye diseases, particularly, allergic conjunctivitis.

Accordingly, this invention provides a new use of the macrolide compounds for preventing or treating eye diseases as mentioned above.

Further, this invention provides a prophylactic or therapeutic agent for eye diseases as mentioned above, which comprises the macrolide compounds.

Still further, this invention provides a method for preventing or treating eye diseases as mentioned above, which comprises administering said macrolide compounds to mammals.

Some of the macrolide compounds used in this invention are known and disclosed, for example, in European Patent Publication No. 0184162 and International Patent Application WO 89/05304.

Those known macrolide compounds include the fermentation products, such as FR-900506, FR-900520, FR-900523 and FR-900525, isolated from microorganisms belonging to genus Streptomyces, such as *Streptomyces tsukubaensis* No. 9993 (FERM BP-927) or *Streptomyces hygroscopicus.* subsp. yakushimaensis No. 7238 (FERM BP-928), and their related compounds prepared from these fermentation products. And new macrolide compounds can be prepared from the above known macrolide compounds in a conventional manner.

These macrolide compounds were indicated inter alia for use in the treatment of rejection to transplantation, autoimmune diseases and infectious diseases caused by pathogenic microorganisms, such as various fungi (*Aspergills fumigatus, Fusarium oxysperum, Trichophyton asteroides,* etc)(e.g.J. Antibiotics, XL(9), 1249–1255, 1987).

The inventors of this invention have surprisingly found that the macrolide compounds mentioned hereinbelow are useful for preventing or treating eye diseases, particularly, allergic conjunctivitis, and also other allergic diseases such as food allergy, allergic rhinitis, etc.

The macrolide compounds used in this invention can be represented by the following general formula (I).

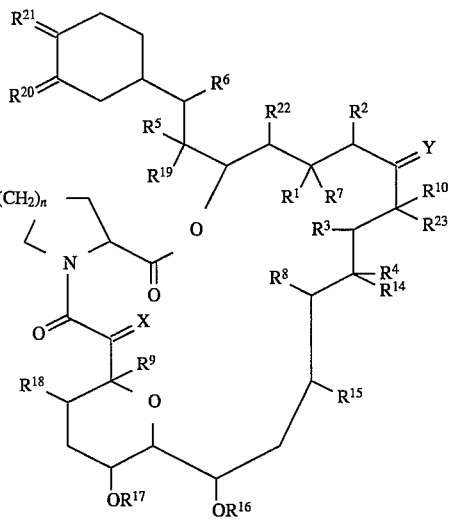

wherein each vicinal pair of substituents [$R^1$ and $R^2$], [$R^3$ and $R^4$], [$R^5$ and $R^6$] independently a) represent two vicinal hydrogen atoms, or b) form a second bond between the vicinal carbon atoms to which they are attached;

in addition to its significance above, $R^2$ may represent an alkyl group;

$R^7$ represents H, OH, protected hydroxy or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O,s (H, OH), (H,H) or —$CH_2O$—;

Y represents O, (H, OH) (H,H) N—$NR^{11}R^{12}$ or N—$OR^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively; $R^{20}$a and $R^{21}$a independently represent OH, O—alkyl or $OCH_2OCH_2CH_2OCH_3$ or $R^{21}$a is protected hydroxy;

in addition, $R^{20}$a and $R^{21}$a may together represent an oxygen atom in an epoxide ring;

n is 1, 2 or 3;

in addition to their significances above Y, $R^{10}$ and $R^{23}$, together with the carbon atoms to which they are attached, may represent a 5- or 6- membered N-, S- or O-containing heterocyclic ring, which may be saturated or unsaturated, and which may be substituted by one or more groups selected from alkyl, hydroxy, alkyl substituted by one or more hydroxyl groups, O—alkyl, benzyl and —$CH_2Se(C_6H_5)$; and pharmaceutically acceptable derivatives thereof.

The specific examples of the definitions of compound (I) and the preferred working modes of the invention are described in detail below.

The term "lower" as used in this specification means, unless otherwise indicated, any number of carbon atoms between 1 and 6, inclusive.

Suitable "alkyl" means straight or branched saturated aliphatic hydrocarbon residue and may include lower alkyl such as methyl, ethyl, propyl, isopropyl, butyl, isobutyl, pentyl, neopentyl, hexyl, and the like.

Suitable "alkenyl" means straight or branched unsaturated aliphatic hydrocarbon residue having one double bond and may include lower alkenyl such as vinyl, propenyl, butenyl, methylpropenyl, pentenyl, hexenyl, and the like.

Suitable "aryl" may include phenyl, tolyl, xylyl, cumenyl, mesityl, naphthyl, and the like.

Suitable examples of the protective group in the "protected hydroxyl group" may include:

1-(lower alkylthio)(lower)alkyl groups such as lower alkylthiomethyl groups (e.g. methylthiomethyl, ethylthiomethyl, propylthiomethyl, isopropylthiomethyl, butylthiomethyl, isobutylthiomethyl, hexylthiomethyl, etc.), more desirably $C_1$—$C_4$ alkylthiomethyl groups, and most desirably methylthiomethyl;

tri-substituted silyl groups such as tri(lower)alkylsilyl groups (e.g. trimethylsilyl, triethylsilyl, tributylsilyl, tert-butyl-dimethylsilyl, tri-tert-butylsilyl, etc.); lower alkyl-diarylsilyl groups (e.g. methyldiphenylsilyl, ethyldiphenylsilyl, propyldiphenylsilyl, tert-butyldiphenylsilyl, etc.), more desirably tri($C_1$—$C_4$)alkylsilyl and $C_1$—$C_4$ alkyldiphenylsilyl groups and most desirably tert-butyldimethylsilyl and tert-butyldiphenylsilyl; and acyl groups such as aliphatic acyl groups, aromatic acyl groups and aliphatic acyl groups substituted by aromatic groups, which are derived from carboxylic acids, sulfonic acids or carbamic acids.

The aliphatic acyl group may includes lower alkanoyl groups which may optionally have one or more suitable substituents such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkoxy(lower)alkanoyl groups which may optionally have one or more appropriate substituents such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl groups having one or more suitable substituents such as carboxy or protected carboxy, for example carboxy(lower)alkylcarbamoyl groups( e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl groups such as tri(lower-)alkylsilyl(lower)alkoxycarbonyl(lower)alkylcarbamoyl groups(e.g. trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

The aromatic acyl group may include aroyl groups which may optionally have one or more suitable substituents such as nitro (e.g. benzoyl, toluoyl, xyloyl, naphthoyl, nitrobenzoyl, dinitrobenzoyl, nitronaphthoyl, etc), arenesulfonyl groups which may optionally have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and so on.

The aromatic group-substituted aliphatic acyl group may include ar(lower)alkanoyl groups which may optionally have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and so on Among the above-mentioned acyl groups, the more desirable acyl groups are $C_1$—$C_4$ alkanoyl groups which may optionally be substituted by carboxy, cyclo($C_5$—$C_6$)alkyloxy-($C_1$—$C_4$)alkanoyl groups having two ($C_1$—$C_4$)alkyl groups in the cycloalkyl moiety, camphorsulfonyl, carboxy($C_1$—$C_4$)alkylcarbamoyl groups, tri($C_1$—$C_4$)alkylsilyl($C_1$—$C_4$)alkoxycarbonyl($C_1$—$C_4$)alkylcarbamoyl groups, benzoyl which may have one or two nitro groups, halogen-substituted benzenesulfonyl groups, phenyl($C_1$—$C_4$)alkanoyl groups having $C_1$—$C_4$ alkoxy and trihalo($C_1$—$C_4$)alkyl groups. Of these groups, the most desirable are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Suitable "5- or 6-membered N-, S- or O-containing heterocyclic ring" may include pyrrolyl, tetrahydrofuryl, and the like.

Preferred embodiments of the Symbols $R^1$ to $R^{10}$, $R^{14}$ to $R^{23}$, X, Y and n are as follows.

$R^1$ and $R^2$ are each hydrogen or combined to form a second bond;

$R^3$ and $R^4$ are combined to form a second bond;

$R^5$ and $R^6$ are combined to form a second bond;

R is hydrogen, hydroxy, 0-lower alkyl such as methoxy or protected hydroxy;

$R^8$ is hydrogen;

$R^9$ is hydroxy;

$R^{10}$ is methyl, ethyl, propyl or allyl;

$R^{14}$, $R^{15}$, $R^{16}$, $R^{17}$, $R^{18}$ and $R^{19}$ are each methyl;

$R^{20}$ is oxo or [$R^{20}$a,H], wherein $R^{20}$a is hydroxy or methoxy;

$R^{21}$ is [$R^{21}$ a,H], wherein $R^{21}$a is hydroxy or protected hydroxy;

$R^{23}$ is hydrogen;

X is oxo, (H,OH) or (H,H);

Y is oxo; and n is 1 or 2.

The pharmaceutically acceptable salt of the compound (I) is a nontoxic salt, which may be the corresponding salt with an inorganic or organic base such as alkali metal salts (e.g. sodium salt, potassium salt, etc.), alkaline earth metal salts (e.g. calcium salt, magnesium salt, etc.), ammonium salt and amine salts (e.g. triethylamine salt, N-benzyl-N-methylamine salt, etc.) and so on.

Referring to compound (I), there may exist conformers or one pair or more of stereoisomers such as optical and geometrical isomers due to the asymmetric carbon or the double bond. Such conformers and isomers also fall within the scope of the invention.

Particularly, the most interesting compound is FR-900506 of the following formula.

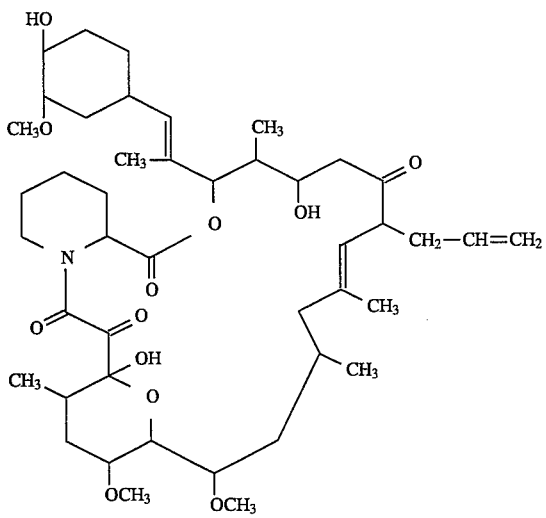

(hereinafter, described as FK506)

As example for showing pharmaceutical activity, the pharmacological test data of the macrolide compounds (I) is illustrated in the following.

Test: Effect of FK 506 on passive anaphylaxis in rat conjunctiva

The diluted rat antiserum (IgE) to ovalbumin in a volume of 50 μl was injected into both palpebral conjunctivas of male Wistar/ST rats aged 6 weeks. Two days later, the rats were challenged intravenously with physiological saline (3 ml/kg) containing 1% ovalbumin and 0.5% Evans blue. The rats were sacrificed 30 min after challenge, and the eye tissues (eyelids and eyeballs) were removed. The intensity of anaphylactic reaction was assessed by measuring the amount of Evans blue extracted from the eye tissues.

Test drug (eye drop) prepared by Example 2 mentioned below was administered topically to the rats 5 and 15 min (Test 1), or 2, 4 and 6 hours (Test 2) before challenge. Control groups were similarly given vehicle. The effect of drug was expressed as percent inhibition of the optical density at 620 nm of the control groups. The result was expressed as the mean ±S.E. and statistical analysis was performed by Dunnett's multiple comparison test.

TABLE

| | Effect of FK 506 on passive anaphylaxis in rat conjunctiva | | |
|---|---|---|---|
| | Optical Density | | Inhibition |
| Sample | Control | Test Sample | (%) |
| Test 1 | 0.300 ± 0.035 (n = 12) | 0.116 ± 0.014** (n = 10) | 61.4 |
| Test 2 | 0.601 ± 0.047 (n = 16) | 0.177 ± 0.028** (n = 10) | 70.5 |

**: $p < 0.01$

The macrolide compounds of the present invention may be administered as pure compounds or mixtures of compounds or preferably, in a pharmaceutical vehicle or carrier.

The pharmaceutical compositions of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external(topical), enteral, intravenous, intramuscular, or parenteral applications. The active ingredient may be compounded, for example, with the usual non-toxic, pharmaceutically acceptable, carriers for tablets, pellets, capsules, eye drops, suppositories, solutions (saline, for example), emulsion, suspensions (olive oil, for example), ointment and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an effective amount sufficient to produce the desired effect upon the process or condition of the disease.

Mammals which may be treated using the method of the present invention include livestock mammals such as cows, horses, etc., domestic animals such as dogs, cats, rats, etc. and humans.

For applying this composition to a human, it is preferable to apply it by external(topical) administration, particularly in the form of eye drops.

While the dosage of therapeutically effective amount of the macrolide compounds varies from and also depends upon the age and condition of each individual patient to be treated, a daily dose of about 0.0001–1000 mg, preferably 0.001–500 mg and more preferably 0.01–100 mg. of the active ingredient is generally given for treating diseases, and an average single dose of about 0.001–0.01mg, 0.2–0.5 mg, 1 mg, 5 mg, 10 mg, 50 mg, 100 mg, 250 mg and 500 mg is generally administered. Daily doses for chronic administration in humans will be in the range of about 0.1–0.3 mg/kg/day.

The following examples are given for the purpose of illustrating the present invention.

EXAMPLE 1

| FK 506 | 1 g |
|---|---|
| Hydroxypropyl methylcellulose 2910 (TC-5R) | 1 g |
| Lactose | 2 g |
| Croscarmellose sodium (Ac-Di-Sol) | 1 g |

The FK 506 (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, maker: Asahi Chemical Industry) were homogeneously suspended to this solution, and then the organic solvent was removed by evaporation. The residual product was dried under reduced pressure for 10 hours by vacuum dryer, milled for 2 minutes by coffee mill and then passed through a sieve (32 mesh) to give the solid dispersion composition of FK 506 (5 g). This composition was capsulated by a conventional manner to provide capsules containing 1 mg or 5 mg of FK 506 per each capsule.

EXAMPLE 2

| FK 506 (fine powder) | 1 mg |
|---|---|
| Polysorbate 80 | 0.5 |
| Polyvinyl alcohol | 2.8 |
| Benzalkonium chloride | 0.1 |
| Sodium chloride | 8.6 |
| pH5.25 Phosphate buffer | to 1 ml |

An aqueous suspending eye drop containing the abovementioned ingredients is prepared according to a conventional manner.

We claim:

1. A method for preventing or treating allergic conjunctivitis, which consists essentially of administering a therapeutically effective amount of FK506 to mammals.

2. A pharmaceutical composition for allergic conjunctivitis, which consists essentially of a therapeutically effective amount of FK506 in admixture with a carrier or excipient.

3. The method as claimed in claim 1, wherein said therapeutically effective amount of FK506 is administered to an eye of a mammal.

4. The pharmaceutical composition as claimed in claim 2, wherein said composition is in the form of an eyedrop.

* * * * *